(12) United States Patent
Daniels

(10) Patent No.: US 10,527,236 B2
(45) Date of Patent: Jan. 7, 2020

(54) LIGHTING APPARATUS

(71) Applicant: OSRAM GmbH, Munich (DE)

(72) Inventor: Martin Daniels, Berlin (DE)

(73) Assignee: ODRAM GmbH, Munich (DE)

( * ) Notice: Subject to any disclaimer, the term of this patent is extended or adjusted under 35 U.S.C. 154(b) by 110 days.

(21) Appl. No.: 15/787,720

(22) Filed: Oct. 19, 2017

(65) Prior Publication Data

US 2018/0112838 A1 Apr. 26, 2018

(30) Foreign Application Priority Data

Oct. 25, 2016 (DE) .......................... 10 2016 220 928

(51) Int. Cl.

| F21K 9/64 | (2016.01) |
|---|---|
| F21V 7/04 | (2006.01) |
| G01J 1/58 | (2006.01) |
| G01N 21/88 | (2006.01) |
| F21Y 113/13 | (2016.01) |
| F21Y 115/10 | (2016.01) |
| F21V 5/00 | (2018.01) |
| F21V 5/04 | (2006.01) |

(52) U.S. Cl.
CPC .................. *F21K 9/64* (2016.08); *F21V 7/04* (2013.01); *G01J 1/58* (2013.01); *G01N 21/88* (2013.01); *F21V 5/008* (2013.01); *F21V 5/04* (2013.01); *F21Y 2113/13* (2016.08); *F21Y 2115/10* (2016.08)

(58) Field of Classification Search
CPC . F21K 9/54; F21S 41/176; F21S 41/16; F21S 45/70; F21V 7/04; G01J 1/58; G01N 21/88
USPC ...................................................... 250/462.1
See application file for complete search history.

(56) References Cited

U.S. PATENT DOCUMENTS

| 8,395,312 B2 * | 3/2013 | Hum .................. H01L 25/0753 |
| | | 313/500 |
| 2015/0023032 A1 | 1/2015 | Kang |
| 2017/0322155 A1* | 11/2017 | Drumm .................. F21S 41/14 |

FOREIGN PATENT DOCUMENTS

| DE | 10 2015 215 742 A1 | 2/2017 |
| EP | 3181995 A1 | 6/2017 |
| WO | 2014037217 A1 | 3/2014 |

OTHER PUBLICATIONS

German Search Report based on application No 10 2016 220 928.0 (8 pages) dated Jul. 17, 2017 (for reference purpose only).

\* cited by examiner

*Primary Examiner* — David P Porta
*Assistant Examiner* — Meenakshi S Sahu

(57) ABSTRACT

A lighting apparatus includes a first semiconductor light source configured to produce a first primary light beam, a second semiconductor light source configured to produce a second primary light beam, a phosphor volume configured to at least partly convert primary light into secondary light, a first deflection element configured to deflect the first primary light beam onto the phosphor volume, a second deflection element configured to deflect the second primary light beam onto the phosphor volume, a first light sensor which is sensitive to at least the primary light, and a second light sensor. The first deflection element is partly transmissive for the first primary light beam. The first light sensor can be irradiated by the component of the primary light beam which is transmitted by the first deflection element. The second light sensor can be irradiated by light which can be emitted by the phosphor volume.

15 Claims, 1 Drawing Sheet

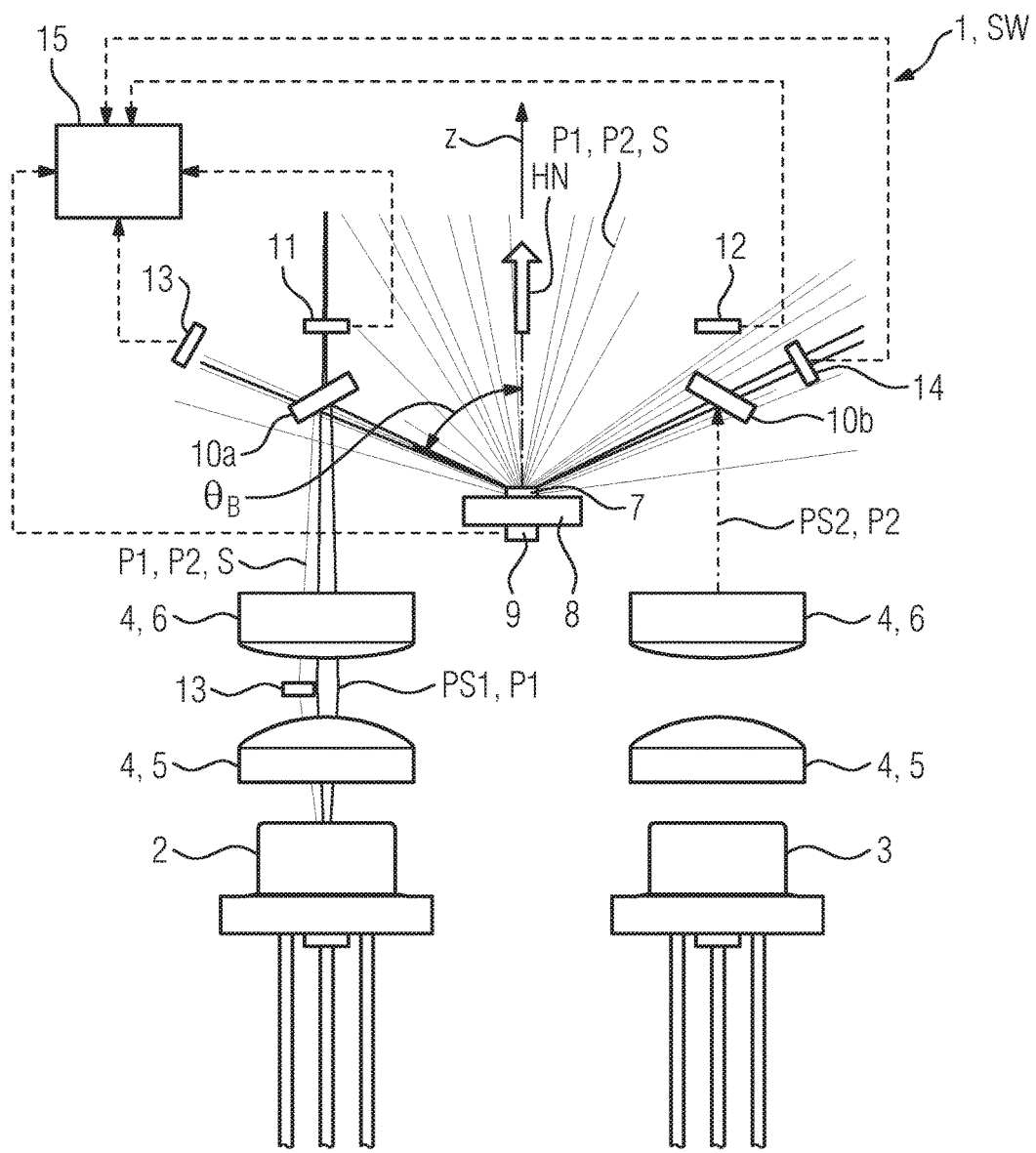

LIGHTING APPARATUS

CROSS-REFERENCE TO RELATED APPLICATION

This application claims priority to German Patent Application Serial No. 10 2016 220 928.0, which was filed Oct. 25, 2016, and is incorporated herein by reference in its entirety.

TECHNICAL FIELD

Various embodiments relate generally to a lighting apparatus having a first semiconductor light source for producing a first primary light beam, a second semiconductor light source for producing a second primary light beam, a phosphor volume for at least partly converting primary light into secondary light, a first deflection element for deflecting the first primary light beam onto the phosphor volume, a second deflection element for deflecting the second primary light beam onto the phosphor volume, a first light sensor, and a second light sensor. Various embodiments are applicable, for example, in projectors, e.g. for vehicles, stage lighting, effect lighting, external lighting, etc.

BACKGROUND

So-called LARP ("laser activated remote phosphor") applications in which a phosphor volume is irradiated by means of a blue primary light emitted by a laser are known. The phosphor volume converts some of the blue primary light into yellow secondary light, as a result of which blue-yellow or white used light with a high luminance is produced. Such LARP arrangements are known for use in automobile headlamps.

On account of the high safety standards in the automotive sector, it is necessary to monitor reliably whether the wavelength conversion operates as expected or whether the direct, blue laser light can emerge from the LARP arrangement. If this is the case, the LARP arrangement can be dimmed or switched off entirely.

SUMMARY

A lighting apparatus includes a first semiconductor light source configured to produce a first primary light beam, a second semiconductor light source configured to produce a second primary light beam, a phosphor volume configured to at least partly convert primary light into secondary light, a first deflection element configured to deflect the first primary light beam onto the phosphor volume, a second deflection element configured to deflect the second primary light beam onto the phosphor volume, a first light sensor which is sensitive to at least the primary light, and a second light sensor. The first deflection element is partly transmissive for the first primary light beam. The first light sensor can be irradiated by the component of the primary light beam which is transmitted by the first deflection element. The second light sensor can be irradiated by light which can be emitted by the phosphor volume.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 1 shows a side view of a lighting apparatus according to a first embodiment.

DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

Various embodiments at least partly overcome the disadvantages of the prior art and, specifically, provide a particularly reliable option for detecting a failure of the phosphor volume.

Various embodiments provide a lighting apparatus having a first semiconductor light source for producing a first primary light beam, a second semiconductor light source for producing a second primary light beam, a phosphor volume for at least partly converting primary light into secondary light, a first deflection element for deflecting the first primary light beam onto the phosphor volume, a second deflection element for deflecting the second primary light beam onto the phosphor volume, a first light sensor which is sensitive to at least the primary light, and a second light sensor, wherein the first deflection element is partly transmissive at least for the primary light beam, the first light sensor can be irradiated by the component of the first primary light beam which is transmitted by the first deflection element and the second light sensor can be irradiated by light which can be emitted by the phosphor volume.

This lighting apparatus is advantageous in that it facilitates a high detection reliability by way of the two light sensors. Moreover, a partial redundancy is provided such that, should one of the light sensors fail, an option for detecting a failure of the phosphor volume still remains available by way of the other sensor. Additionally, such a lighting apparatus is compact and reliably implementable. The use of a plurality of semiconductor light sources for irradiating the same phosphor volume yields the further effect in that the service life thereof can be increased by reducing the operating current thereof. This also increases reliability because, should one semiconductor light source fail, the other semiconductor light source can at least partly compensate this failure. Moreover, the light sensors thus can be tested and/or calibrated separately.

The semiconductor light source can have at least one semiconductor laser and/or at least one light-emitting diode. There may be at least one optical unit for beam guiding and/or beam shaping of the associated primary light beam optically downstream of the semiconductor light source, for example at least one lens, for example a Fresnel lens, at least one collimator, etc.

The primary light beam is produced by means of a respective primary light that can be emitted by the associated semiconductor light source. In the case of a laser, the primary light can also be referred to as pump light. By way of example, the primary light can be ultraviolet or blue primary light.

The phosphor volume or converter volume has at least one phosphor that is suitable to convert, at least in part, incident primary light into secondary light with a different wavelength. If a plurality of phosphors are present, these can produce secondary light having wavelengths that differ from one another. The wavelength of the secondary light can be longer (a so-called "down conversion") or shorter (a so-called "up conversion") than the wavelength of the primary light. By way of example, blue primary light can be converted into green, yellow, orange or red secondary light by means of a phosphor. In the case of an only partial wavelength conversion, the phosphor volume emits a mixture of secondary light and non-converted primary light, which can serve as used light. By way of example, white used light can be produced from a mixture of blue, non-converted primary light and yellow secondary light. However, a complete conversion is also possible; here, the primary light is no longer present, or only present in negligible amounts, in the used light. By way of example, a degree of conversion depends on a thickness and/or a phosphor concentration of the phosphor. If a plurality of phosphors are present, secondary light components with different spectral compositions can be produced from the primary light, for example yellow and red secondary light. By way of example, the red secondary light may be used to provide the used light with a warmer hue, e.g. so-called "warm white". If a plurality of phosphors are present, at least one phosphor may be suitable for a further wavelength conversion of the secondary light, e.g. a wavelength conversion of green secondary light into red secondary light. Such light that was wavelength converted another time from a secondary light may also be referred to as "tertiary light".

The phosphor body can have phosphor particles, e.g. powder particles, which are embedded in a distributed manner in a light-transmissive matrix material. By way of example, the matrix material can have silicone, epoxy resin or glass. The phosphor body also may include or essentially consist of an integral wavelength-converting body, for example of a wavelength-converting ceramic (converter ceramic) such as YAG:Ce, LuAG, $LiEuMo_2O_8$ or $Li_3Ba_2Eu_3(MoO_4)_8$. The phosphor body can be a platelet-shaped phosphor body.

The first deflection element can be a partly transmissive deflection mirror, e.g. a silver-coated mirror or a dichroic mirror. In a development, the first deflection element can be partly transmissive only for the primary light (and be opaque to the secondary light). This yields the advantage that the first light sensor can determine an intensity of the primary light particularly accurately since no extraneous component from the secondary light impinges on the first light sensor. Then, this development can also be implemented without further disadvantages using a simple light sensor with broadband sensitivity. In another development, the first deflection element can be partly transmissive for the primary light and partly transmissive or completely transmissive for the secondary light. This may yield the effect that the deflection element can have a particularly simple embodiment.

The first light sensor can be a light sensor, for example a brightness sensor, that is only sensitive to the primary light (and not to the secondary light as well). Alternatively, the first light sensor can be a light sensor that is sensitive to the primary light and to the secondary light. The first light sensor can be irradiated by at least some of the primary light transmitted through the first deflection element (i.e. by at least some of the transmission component of the primary light beam). If, for example, the first primary light beam that is emitted by the first semiconductor light source impinges on the deflection element on the front side, it is deflected onto the phosphor volume there with a certain reflectance R (e.g. of 95% or more). A smaller portion of the primary light beam passes through the deflection element with a certain transmittance (e.g. of 5% or less) and then, at least in part, onto the first light sensor disposed optically downstream of the deflection element.

The second light sensor can be a light sensor that is only sensitive to the secondary light (and not to the primary light as well), a light sensor that is only sensitive to the primary light (and not to the secondary light as well) or a light sensor that is sensitive to the primary light and to the secondary light.

In a development, the deflection mirrors deflect the primary light rays onto the phosphor volume at a large angle of incidence. In various embodiments, the incoming radiation at the large angle of incidence can increase an input coupling efficiency. The incoming radiation at a large angle of incidence with a plurality of semiconductor light sources moreover facilitates particularly reliable and redundant monitoring of the phosphor volume as this opens up, in a very simple manner, the option of not emitting the primary light rays in a direct and unhindered fashion should the phosphor volume be missing or damaged.

In a further development, the primary light rays, or their chief axis of highest luminous intensity, are incident on the phosphor volume at the Brewster angle. This can increase, particularly strongly, the input coupling efficiency. In various embodiments, the Brewster angle can lie between 45° and 65°, for example between 60° and 62°.

Moreover, in a development, the deflection elements are arranged in a spatial region which is angled by at least 45° in relation to a chief axis of highest luminous intensity of the used light emitted by the phosphor volume. An effect obtained hereby may be that of the deflection elements only blocking a small component of the used luminous flux emitted overall by the phosphor volume. In various embodiments, the aperture angle can correspond approximately to the Brewster angle. As a consequence, a range between 45° and 65° is generally preferred.

The deflection mirrors can be integrated into a more complex light-guiding glass part, can be used to adjust the direction of the associated primary light beam and/or can be embodied as a design element (e.g. be integrated in a metal flap or in a reflector, etc.).

The fact that the second light sensor can be irradiated by light that can be emitted by the phosphor volume may encompass the case where the second light sensor can be irradiated by secondary light and/or by non-converted primary light.

In a configuration, the second deflection element is at least partly transmissive for light which can be emitted by the phosphor volume. Here, in a development, the second deflection element can be transmissive for the secondary light only, to be precisely partly transmissive or wholly transmissive (transparent), but opaque to the primary light. This may achieve the effect that the second light sensor can determine an intensity of the secondary light particularly accurately as no extraneous component resulting from non-converted primary light impinges on the first light sensor. In a further development, the second deflection element can be transmissive for the secondary light and partly transmissive for the primary light. This may yield the effect that the second light sensor can receive a particularly strong luminous flux of the primary light should the phosphor volume be damaged, facilitating a particularly reliable failure detection. In an even further development, the second deflection element can be opaque to the secondary light and partly transmissive for the primary light. Here too, a particularly strong luminous flux of the primary light can be detected in the case of damage.

Additionally, the second light sensor can be irradiated by light (secondary light and/or primary light) which can be emitted by the phosphor volume and which can be transmitted by the second deflection element. As a result, the second light sensor is downstream of the second deflection element in relation to the light emitted by the phosphor volume, as a result of which shadowing of the used light emitted by the phosphor volume can be kept particularly low.

In an even further configuration, the second deflection element is partly transmissive for the second primary light beam and at least partly transmissive for light which can be emitted by the phosphor volume, and the lighting apparatus has a further first light sensor which can be irradiated by the portion of the second primary light beam which is transmitted by the second deflection element. As a result, it may be possible to reliably measure the brightness or luminance of both primary light beams independently of one another. Their brightnesses may significantly deviate from one another, either due to production or this is set to be so in a targeted manner. Additionally, such a brightness or luminance of the primary light beams is measurable in the case of selectively activated or deactivated semiconductor light sources.

In a further configuration, the first deflection element is partly transmissive for the first primary light beam and at least partly transmissive for light which can be emitted by the phosphor volume, and the lighting apparatus has a further second light sensor which can be irradiated by the light of the phosphor volume which is transmitted by the first deflection element. As a result, a more reliable detection of the light emitted by the phosphor volume is facilitated. In various embodiments, damage to the phosphor volume can be determined in two ways, independently of one another, namely by way of the first light sensor and the second light sensor and, independently thereof, by way of the further first light sensor and the further second light sensor.

In an alternative or additional configuration, the lighting apparatus has at least one (possibly more than one) second light sensor which can be irradiated by light which is reflected at the first deflection element and/or at the second deflection element and which can be emitted by the phosphor volume. This may yield the effect that a brightness or luminance of the used light or used light component which is detected by this second light sensor is higher than in the case of an arrangement downstream of the associated deflection element. Thus, by means of a second light sensor, it is possible to detect, alternatively or together, the portion of the used light passing through the deflection element or the portion of the used light or of a used light component (primary light, secondary light) reflected by the deflection element.

In a further configuration, at least one second light sensor is also sensitive to the primary light and situated downstream of the phosphor volume in an optical path of the primary light beam. This may achieve the effect that, should the phosphor volume be damaged, the primary light beam which is no longer at least partly converted or scattered in that case impinges on the second light sensor. Thus, a particularly strong sensor signal can be produced, which can capture the damage to the phosphor volume particularly reliably.

In a further configuration, the first semiconductor light source and the second semiconductor light source are aligned symmetrically in relation to the phosphor volume. This facilitates a particularly compact arrangement. By way of example, the semiconductor light sources can be arranged with mirror symmetry in relation to the phosphor volume or arranged by 180° with rotational symmetry in relation to the phosphor volume. This can also be referred to as an opposite arrangement.

In a development, two first light sensors and two second light sources are aligned symmetrically in relation to the phosphor volume, in particular in an opposite arrangement, if said two first light sensors and two second light sensors are present.

In a further development, the first semiconductor light source and the second semiconductor light source are aligned parallel to one another.

In a further development, the main axes of highest luminous intensity of the primary light beams and of the used light emitted by the phosphor volume are arranged parallel to one another.

In a further development, the lighting apparatus has a plurality of sets of mutually opposing arrangements consisting in each case of two semiconductor light sources, two first light sensors, two second light sensors and two deflection elements. In various embodiments, these plurality of sets use the same phosphor volume. In various embodiments, the components of the sets are angled equidistantly around the phosphor volume. In the case of two sets (together with a total of four semiconductor light sources, etc.), the components thereof can be rotated by e.g. 90° about an axis around the phosphor volume; this rotation is 60° in the case of three sets, etc.

Moreover, in one configuration, the first semiconductor light source and the second semiconductor light source are individually activatable. This facilitates a particularly high flexibility when forming an emission pattern of the used light.

Particularly high flexibility when forming an emission pattern of the used light can also be obtained by the configuration where the first primary light beam and the second primary light beam have a different profile form and/or profile dimension.

In a development, the lighting apparatus is configured to vary a form and/or a luminous spot produced on the phosphor volume. By way of example, this can be implemented by virtue of a form and/or dimension of the profile of the primary light beams being variable. Alternatively, or additionally, the luminous spots produced on the phosphor volume by the primary light beams are not exactly congruent, and so the emission pattern can be changed in terms of its form by different activations of the semiconductor light sources.

The semiconductor light sources can be operable in a pulsed and/or amplitude-modulated manner. In a development, different semiconductor light sources are operable or operated differently, for example with different pulse and/or amplitude characteristics. By way of example, different semiconductor light sources can be operated sequentially or overlapping in time, for example by way of a setting of a respective pulsed operation. In various embodiments, different semiconductor light sources can be operated alternately or intermittently.

In another development, the power of the primary light beams emitted by the semiconductor light sources can be scaled or dimmed, in particular individually scaled.

In a further configuration, the lighting apparatus has a temperature sensor for sensing or monitoring a temperature of the phosphor volume. The temperature sensor can be used for avoiding overheating, in particular a thermal destruction, of the phosphor volume.

In a further configuration, the phosphor volume lies on a reflecting carrier. The reflecting arrangement has significant advantages, both thermally and from a safety point of view, in relation to a transmitting arrangement—which in principle can also be used. By way of example, the heat converted in the phosphor volume can be dissipated significantly more efficiently than in the case of the transmitting arrangement. Additionally, temperature monitoring of the phosphor volume can be implemented significantly more easily and more directly. For particularly good thermal compartmenting, the carrier may consist of a metal or ceramic. The side of the carrier facing the phosphor volume is mirrored for a particularly high light yield. The temperature sensor can be arranged on a side of the carrier facing away from the phosphor volume.

In a further configuration, the first semiconductor light source and the second semiconductor light source emit primary light (beams) with different wavelengths or pump wavelengths. This may yield the effect that the associated primary light beams and/or the primary light emitted by the phosphor volume are distinguishable. This in turn may yield effects when searching for a fault. In various embodiments, there also can be an excitation of the phosphor volume by means of different degrees of absorption and/or different degrees of efficiency, which may reduce saturation. By way of example, the different wavelengths can be distinguished by light sensors which have appropriate edge filters. By way of example, the different wavelengths can correspond to blue light, for example with 445 nm, 460 nm or 473 nm. However, the first semiconductor light source and the second semiconductor light source also can emit primary light (beams) with the same spectral composition, in particular the same wavelength.

In a further configuration, the lighting apparatus has a data processing unit connected to the light sensors, said data processing unit being configured to evaluate a sensor signal from at least a first light sensor and at least a second light sensor in respect of the presence of damage to the phosphor volume. By way of example, if the phosphor volume is present and not damaged, light emitted thereby will be incident on the second light sensor. This light can be the used light (i.e. a mixture of the secondary light and the non-converted primary light) or only a component thereof (e.g. the primary light or the secondary light). If the phosphor volume falls, this luminous flux can become significantly smaller in the case of an unchanging primary light beam if the second light sensor is not situated in the light path of the primary light beam that emerges in that case. Alternatively, this luminous flux can become significantly larger in the case of an unchanging primary light beam if the second light sensor is situated in the light path of the primary light beam resulting in that case and if it is sensitive to the primary light. Thus, it is possible to deduce the presence of damage to the phosphor volume from a strength of a change in the sensor signal of the second light sensor, normalized to the strength of the sensor signal of the first light sensor. The damage may include, for example, the formation of a crack, a partial removal or a complete removal of the phosphor volume.

In a further configuration, the lighting apparatus is a projector or part of a projector (e.g. a light production module). Here, the high luminance is particularly useful. The projector can be a vehicle headlamp, a spotlight for stage illumination, a spotlight for external illumination, a spotlight for effect illumination, etc. The vehicle can be a motor vehicle (e.g. a motor vehicle such as an automobile, a truck, a bus, etc. or a motorbike), a train, a watercraft (e.g. a boat or ship) or an aircraft (e.g. an airplane or a helicopter).

The lighting apparatus 1 can be a module of a projector SW. The lighting apparatus 1 has a first semiconductor light source in the form of a first laser diode 2 for producing a first primary light beam PS1. The first primary light beam PS1 is emitted in the z-direction z and it consists of blue primary light P1. The lighting apparatus 1 also has a second semiconductor light source in the form of a second laser diode 3 for producing a second primary light beam PS2 (only indicated). The second primary light beam PS2 is likewise emitted in the z-direction z and it consists of blue primary light P2. The spectral characteristic, e.g. a dominant wavelength, of the two primary light beams PS1 and PS2 can be the same or different. Additionally, a profile form and/or profile dimension of the two primary light beams PS1 and PS2 can be the same or different.

Disposed downstream of both the laser diodes 2, 3 there respectively is one optical unit 4, in this case with two lenses 5 and 6 that are optically connected in series in an exemplary manner, for focusing the primary light beams PS1 and PS2 onto a phosphor volume in the form of e.g. a ceramic phosphor platelet 7. The phosphor platelet 7 lies on a reflecting carrier 8 made of metal. The carrier 8 is mirrored on the surface facing the phosphor platelet 7 and it may have a temperature sensor 9 on the surface that faces away from the phosphor platelet 7. The phosphor platelet 7 is able to partly convert incident primary light P1, P2 into secondary light S, e.g. blue primary light P1, P2 into yellow secondary light S. A main axis HN of the mixed light P1, P2, S that is emitted by the phosphor platelet 7 as used light is perpendicular to a surface of the phosphor platelet 7 and hence is likewise parallel to the z-axis in this case.

Since the laser diodes 2 and 3 are laterally offset in relation to the phosphor platelet 7 and do not radiate directly onto the phosphor platelet 7, use is made of two deflection elements in the form of partly transmissive deflection mirrors 10a and 10b, respectively, for deflecting the respective primary light beams P1 and P2 onto the phosphor platelet 7. In various embodiments, the deflection mirrors 10a, 10b are partly transmissive for the primary light P1, P2 and partly transmissive or completely transmissive for the secondary light S. Here, the deflection mirrors 10a, 10b are aligned in such a way that the primary light beams P1 and P2 are incident on the phosphor platelet 7 at the Brewster angle $\theta_B$.

The deflection mirrors 10a, 10b are situated in a spatial region that lies outside of a cone (not plotted here) attached to the phosphor platelet 7, said cone having an aperture angle of 45° about the main axis HN. In various embodiments, the aperture angle can approximately correspond to the Brewster angle. As a consequence, a range between 45° and 65° is generally preferred.

The lighting apparatus 1 further has a first light sensor 11 that is at least sensitive to the primary light P1, a further first light sensor 12 that is at least sensitive to the primary light P2, a second light sensor 13 and a further second light sensor 14. The light sensors 13 and 14 can be sensitive to the primary light P1 and/or P2, to the secondary light S and to both the primary light P1, P2 and the secondary light S. The light sensors 11 to 14 can be, or have, e.g. photodiodes, said photodiodes optionally having wavelength-dependent filters (e.g. edge filters) placed upstream thereof.

The first light sensors 11 and 12 are arranged downstream of the respective deflection mirrors 10a and 10b in relation to the incident primary light beams P1 and P2. While a large majority (e.g. more than 95%) of the incident primary light beams P1 and P2 is deflected onto the phosphor platelet 7 by the deflection mirrors 10a and 10b, a small portion (e.g. 5% or less) is transmitted by the deflection mirrors 10a and 10b and radiates on the light sensors 11 and 12.

The second light sensors 13 and 14 are arranged downstream of the respective deflection mirrors 10a and 10b in relation to the used light P1, P2, S that is emitted by the phosphor platelet 7. The deflection mirrors 10a and 10b can be partly or wholly transmissive for the secondary light S. Consequently, the primary light P1, P2 is transmitted (in part) through the deflection mirrors 10a and 10b and the secondary light S is transmitted (completely or in part) through the deflection mirrors 10a and 10b and said primary light P1, P2 and secondary light S can irradiate the light sensors 14 and 13 having been emitted by the phosphor platelet 7.

The second light sensors 13 and 14 situated downstream of the deflection mirrors 10a and 10b are positioned in such a way that they are situated in the light path of the respective primary light beam PS2 and PS1 if the phosphor platelet 7 falls away.

As an alternative or in addition to the position behind the respective deflection mirror 10a and/or 10b, the second light sensor 13 and/or 14 can be situated at a point onto which used light P1, P2, S emitted by the phosphor platelet 7 has been reflected by means of the deflection mirror 10. By way of example, such a point can be situated between the lenses 5 and 6, permitting a particularly compact design, as shown in an exemplary manner for the second light sensor 13.

The lighting apparatus moreover has a data processing unit 15 that is connected to the light sensors 11 to 14 and that is configured to evaluate the sensor signals from the light sensors 11 to 14 for the presence of damage to the phosphor platelet 7 (including the removal thereof).

In the normal case, the light sensors 11 and 12 can detect the luminance or the luminous flux of the portion of the primary light beams PS1 and PS2 transmitted through the deflection mirrors 10a and 10b. If the deflection mirrors 10a and 10b are also transmissive for the secondary light S and the light sensors 11 and 12 are sensitive to the secondary light S, an orientation of the light sensors 11 and 12 can be set in such a way that a portion of the incident secondary light S is practically negligible. In the case of sensitivity to the primary light P1, P2 and to the secondary light S, the light sensors 13 and 14 detect a corresponding luminous flux that is transmitted through the deflection mirrors 10b and 10a. By way of example, the data processing unit 15 can monitor a ratio of the sensor signals of pairs of light sensors 11 and 14, and 12 and 13.

By way of example, if the phosphor platelet 7 detaches from the carrier 8 in the case of damage or if a tear forms in the phosphor platelet 7, no secondary light S or less secondary light S is produced in this case and the primary light beams PS1 and PS2 are incident on the deflection mirrors 10b and 10a with a higher intensity than in the fault-free case. In the case where the deflection mirrors 10a, 10b are not transmissive for the primary light P1, P2 and/or the light sensors 13 and 14 are not sensitive to the primary light P1, P2, the sensor signal tapped at the light sensors 13 and 14 drops noticeably without the luminous flux of the primary light beams PS1, PS2 also reducing. As a result, damage to the phosphor platelet 7 can be detected. In the case where the deflection mirrors 10a, 10b are transmissive for the primary light P1, P2 and the light sensors 13 and 14 are sensitive to the primary light P1, P2, the sensor signal tapped at the light sensors 13 and 14 increases significantly, without the luminous flux of the primary light beams PS1, PS2 also increasing. Damage to the phosphor platelet 7 can also be detected thereby.

Even though the invention was illustrated more closely and described in detail by the embodiments described above, the invention is not limited thereto and other variations may be derived therefrom by a person skilled in the art, without departing from the scope of protection of the invention.

Generally, "a(n)", "one", etc. may be understood to mean a singular or a plural, e.g. in the sense of "at least one" or "one or more", etc., as long as this is not explicitly excluded, e.g. by the expression "exactly one", etc.

Moreover, a numerical indication may encompass exactly the indicated number and also a customary tolerance range, as long as this is not explicitly excluded.

LIST OF REFERENCE SIGNS

Lighting apparatus 1
First laser diode 2
Second laser diode 3
Optical unit 4
Lens 5
Lens 6
Phosphor platelet 7
Carrier 8
Temperature sensor 9
First deflection mirror 10a
Second deflection mirror 10b
First light sensor 11
First light sensor 12
Second light sensor 13
Second light sensor 14
Data processing unit 15
Main axis HN
Primary light P1
Primary light P2
First primary light beam PS1
Second primary light beam PS2
Projector SW
z-direction Z
Brewster angle $\theta_B$ While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:
1. A lighting apparatus, comprising:
a first semiconductor light source configured to produce a first primary light beam;
a second semiconductor light source configured to produce a second primary light beam;
a phosphor volume configured to at least partly convert primary light into secondary light;
a first deflection element configured to deflect the first primary light beam onto the phosphor volume;
a second deflection element configured to deflect the second primary light beam onto the phosphor volume;
a first light sensor which is sensitive to at least the primary light; and
a second light sensor;

wherein the first deflection element is partly transmissive for the first primary light beam;

wherein the first light sensor can be irradiated by a component of the primary light beam which is transmitted by the first deflection element; and wherein the second light sensor can be irradiated by light which can be emitted by the phosphor volume.

2. The lighting apparatus of claim 1, wherein the second deflection element is at least partly transmissive for light which can be emitted by the phosphor volume; and wherein the second light sensor can be irradiated by light which can be emitted by the phosphor volume and which can be transmitted by the second deflection element.

3. The lighting apparatus of claim 1, wherein the second light sensor can be irradiated by light which can be emitted by the phosphor volume and which can be transmitted by the second deflection element the second deflection element is partly transmissive for the second primary light beam and at least partly transmissive for light which can be emitted by the phosphor volume; and wherein the second light sensor can be irradiated by light which can be emitted by the phosphor volume and which can be transmitted by the second deflection element.

4. The lighting apparatus of claim 1, wherein the second light sensor can be irradiated by light which can be emitted by the phosphor volume and which can be transmitted by the second deflection element the first deflection element is at least partly transmissive for light which can be emitted by the phosphor volume; and wherein the second light sensor can be irradiated by light which can be emitted by the phosphor volume and which can be transmitted by the second deflection element.

5. The lighting apparatus of claim 1, wherein the lighting apparatus has at least one second light sensor which can be irradiated by light which is reflected at the first deflection element and which can be emitted by the phosphor volume.

6. The lighting apparatus of claim 1, wherein the lighting apparatus has at least one second light sensor which can be irradiated by light which is reflected at the second deflection element and which can be emitted by the phosphor volume.

7. The lighting apparatus of claim 1, wherein at least one second light sensor is sensitive to the primary light and situated downstream of the phosphor volume in an optical path of a primary light beam.

8. The lighting apparatus of claim 1, wherein the lighting apparatus has a temperature sensor configured to sense a temperature of the phosphor volume.

9. The lighting apparatus of claim 1, wherein the phosphor volume lies on a reflecting carrier.

10. The lighting apparatus of claim 1, wherein the first semiconductor light source and the second semiconductor light source are aligned symmetrically in relation to the phosphor volume.

11. The lighting apparatus of claim 1, wherein the first semiconductor light source and the second semiconductor light source are individually activatable.

12. The lighting apparatus of claim 1, wherein the first semiconductor light source and the second semiconductor light source emit primary light with different wavelength.

13. The lighting apparatus of claim 1, wherein the first primary light beam and the second primary light beam have a different profile form.

14. The lighting apparatus of claim 1, further comprising:

a data processing unit which is connected to the light sensors, said data processing unit being configured to evaluate a sensor signal of at least one first light sensor and at least one second light sensor for a presence of damage to the phosphor volume.

15. The lighting apparatus of claim 1, wherein the lighting apparatus is a projector or a part of a projector.

* * * * *